United States Patent
Sauer et al.

[11] Patent Number: 5,839,639
[45] Date of Patent: Nov. 24, 1998

[54] COLLAPSIBLE ANVIL ASSEMBLY AND APPLICATOR INSTRUMENT

[75] Inventors: Jude S. Sauer; Alex Kobilansky, both of Pittsford; Theodore J. Tiberio, Hilton; Jeffrey M. Shaw, Livonia, all of N.Y.

[73] Assignee: LaserSurge, Inc., Rochester, N.Y.

[21] Appl. No.: 516,474

[22] Filed: Aug. 17, 1995

[51] Int. Cl.⁶ .................................................. A61B 17/068
[52] U.S. Cl. ...................... 227/175.1; 227/19; 227/153; 227/176.1; 227/179.1
[58] Field of Search .................................. 606/139, 153; 227/19, 175.1, 176.1, 178.1, 179.1, 180.1, 151, 152, 153, 154, 155

[56] References Cited

U.S. PATENT DOCUMENTS

| | | | |
|---|---|---|---|
| 4,505,414 | 3/1985 | Filipi | 227/19 |
| 4,700,703 | 10/1987 | Resnick et al. | 227/19 |
| 4,752,024 | 6/1988 | Green et al. | 227/19 |
| 4,893,622 | 1/1990 | Green et al. | 227/180.1 |
| 4,903,697 | 2/1990 | Resnick et al. | 227/178.1 |
| 5,119,983 | 6/1992 | Green et al. | 227/179.1 |
| 5,368,215 | 11/1994 | Green et al. | 227/179.1 |
| 5,522,534 | 6/1996 | Viola et al. | 227/179.1 |

*Primary Examiner*—Scott A. Smith
*Attorney, Agent, or Firm*—Cumpston & Shaw

[57] ABSTRACT

A collapsible anvil assembly and applicator instrument for use with a surgical stapler. The collapsible anvil assembly includes an anvil shaft and a plurality of anvil segments, having staple clinching buckets thereon, flexibly affixed to the anvil shaft which are movable between a collapsed or radially inwardly deflected condition and an expanded or radially outwardly deflected condition. Immobilizing means in the form of an axially slidable locking ring is provided to fix and maintain the anvil segments in the expanded condition. Mounting element are also provided for subsequent detachable mounting of the anvil assembly on a surgical stapler. The collapsible anvil assembly may also include a suction purse stringing device which attracts and holds a surrounding tissue section within the anvil segments. Additionally, an axially slidable tissue holding ring or snap cap is provided to lock the held tissue section within the anvil segments.

17 Claims, 13 Drawing Sheets

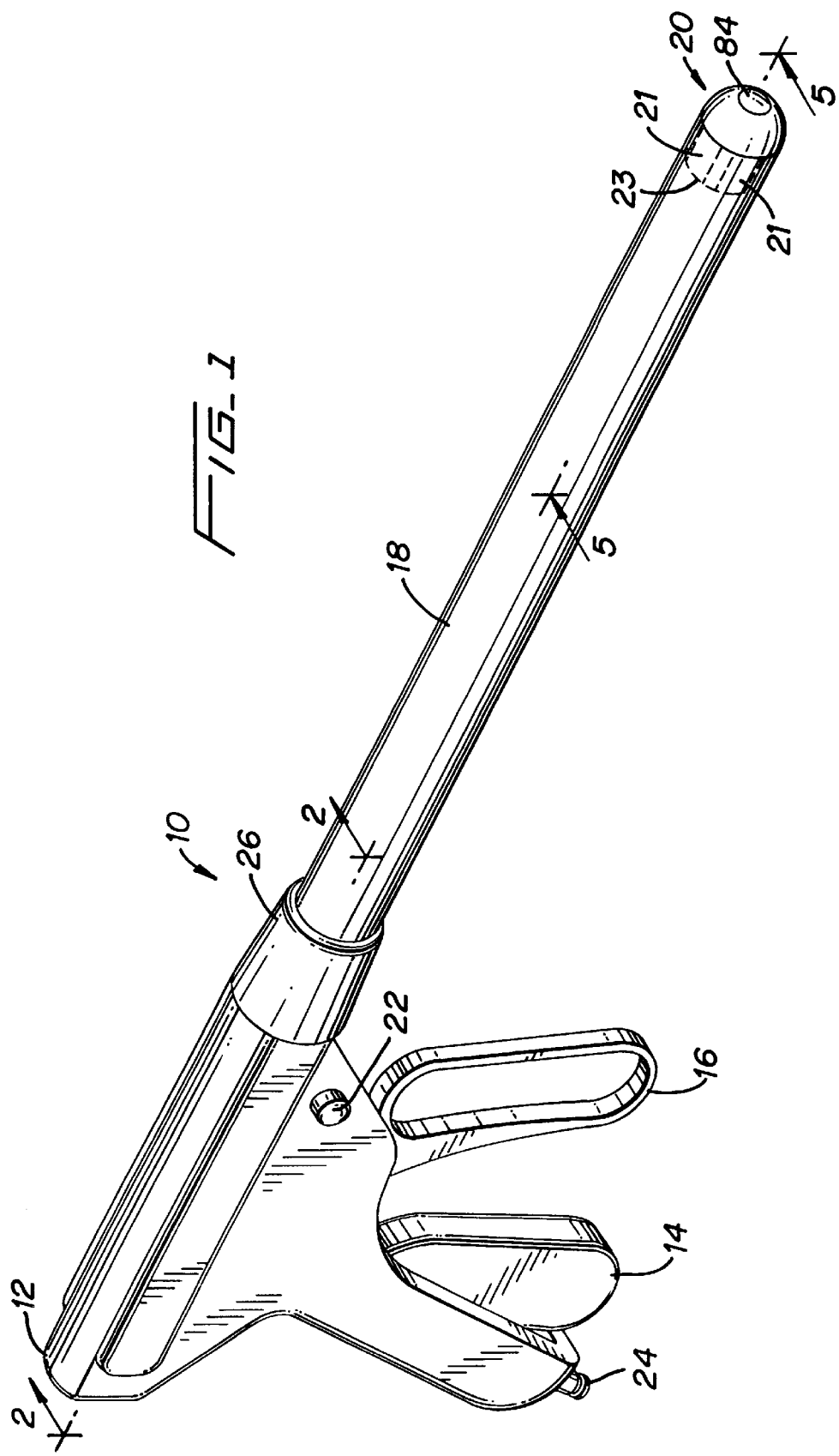

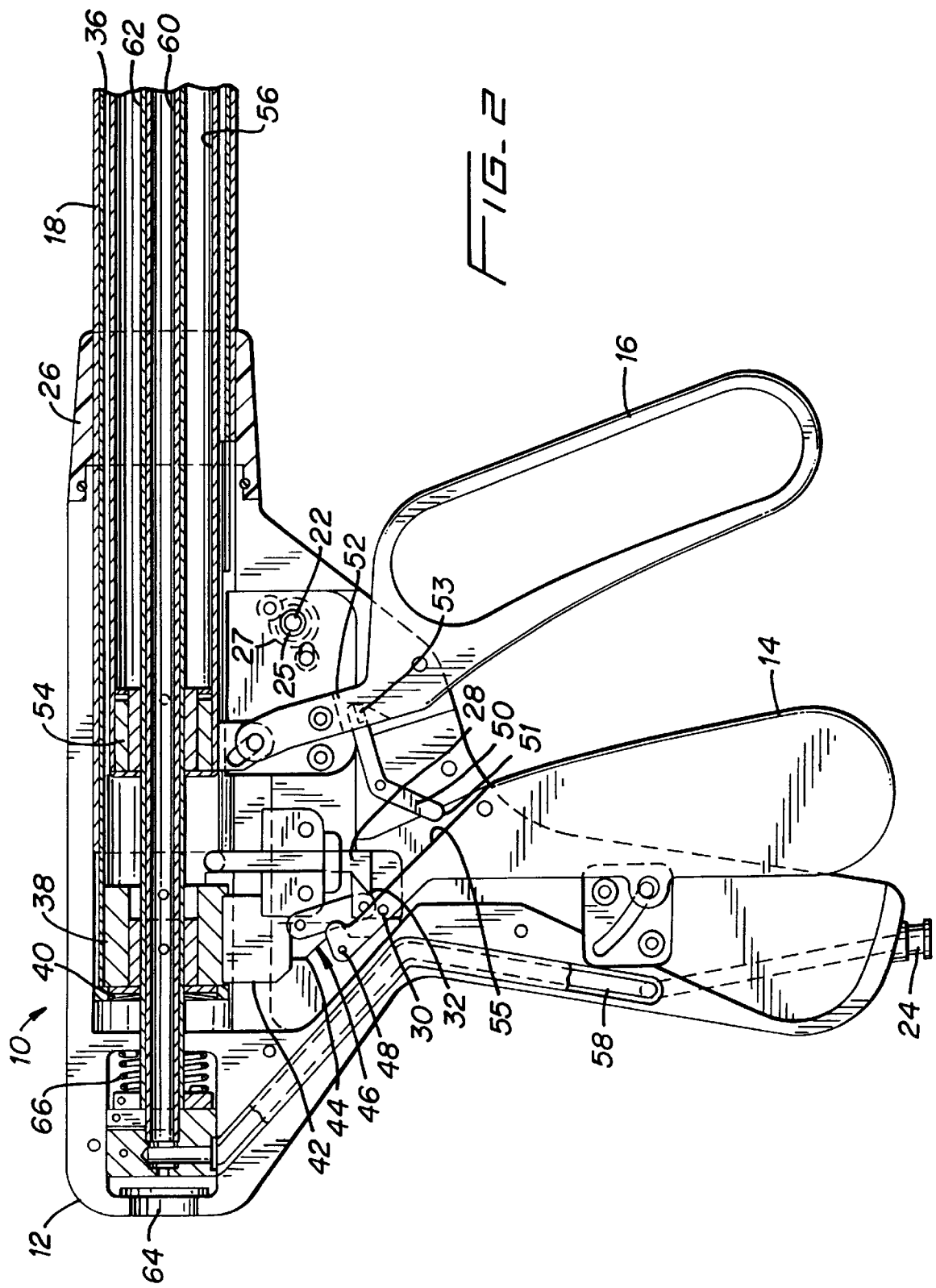

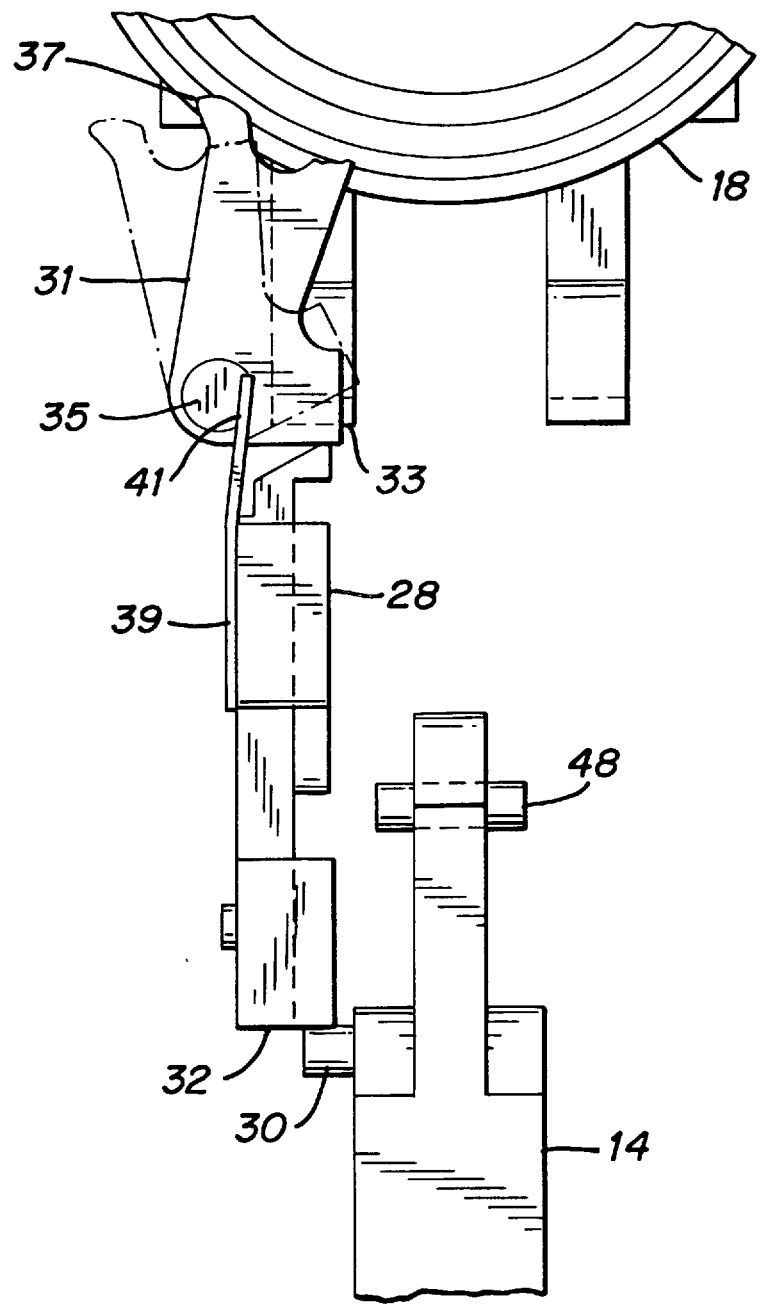

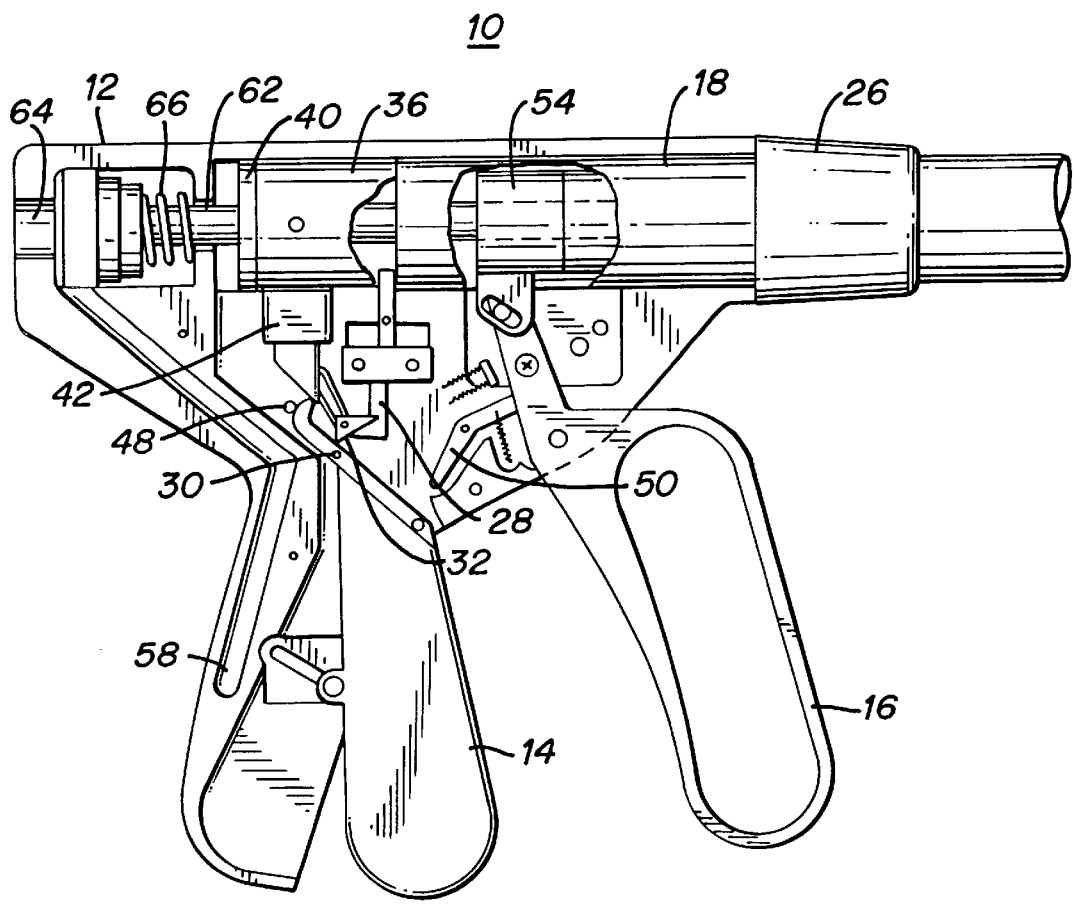
FIG_4

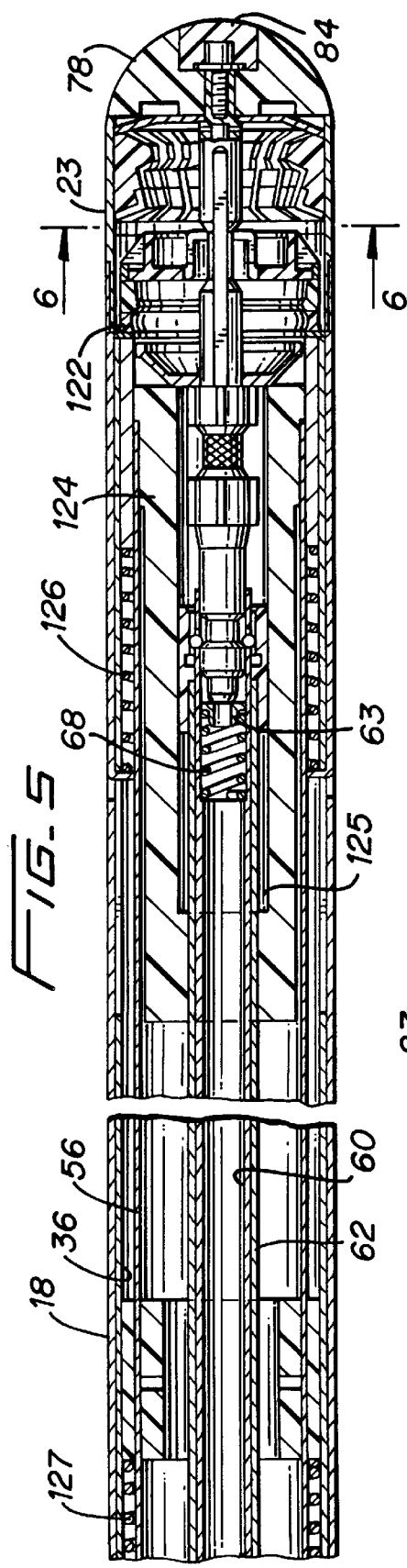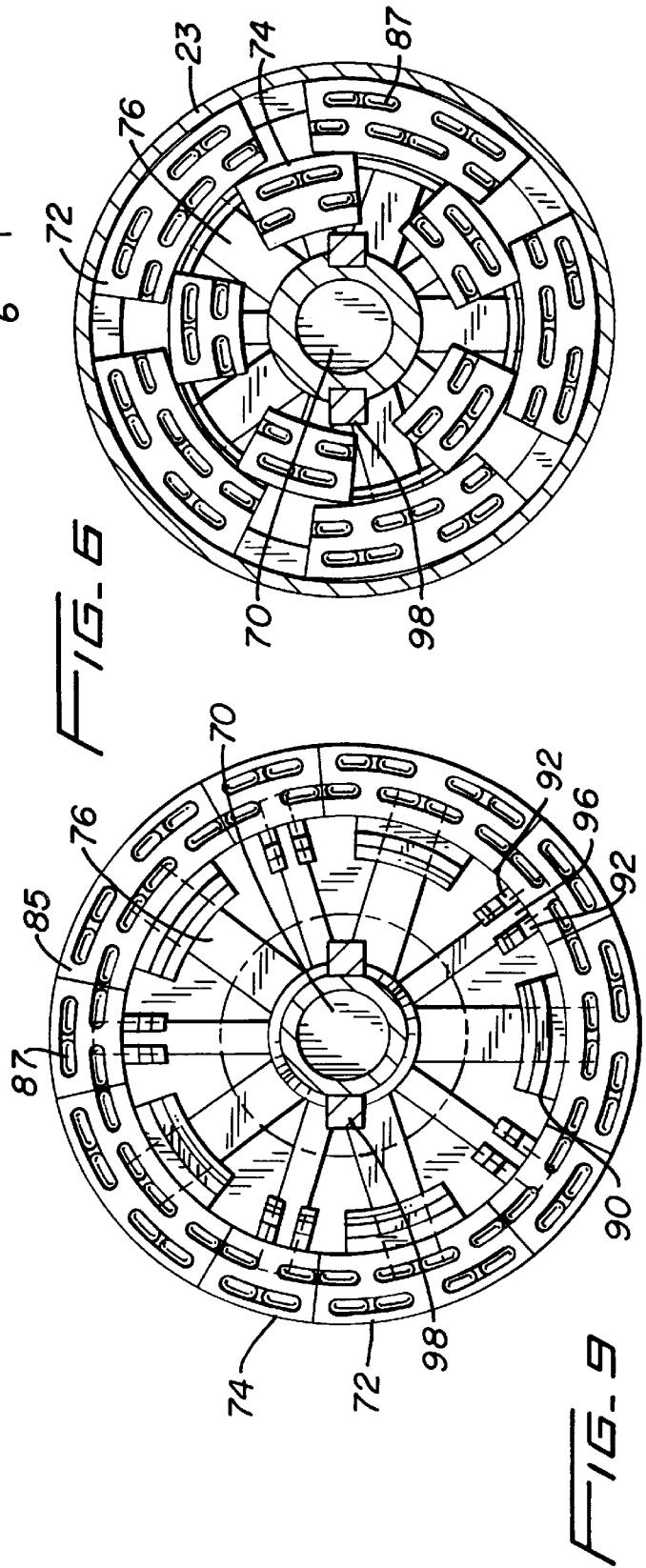

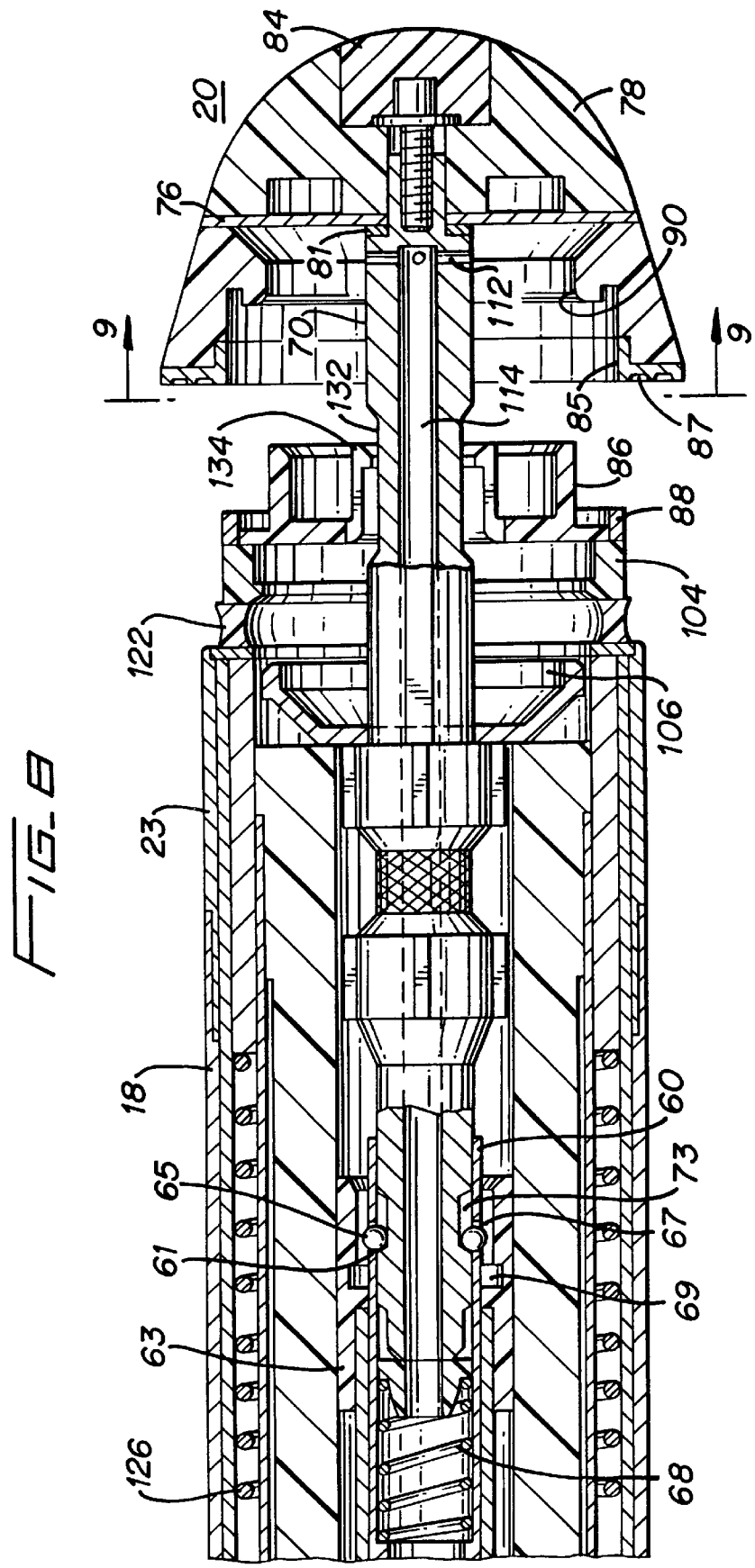

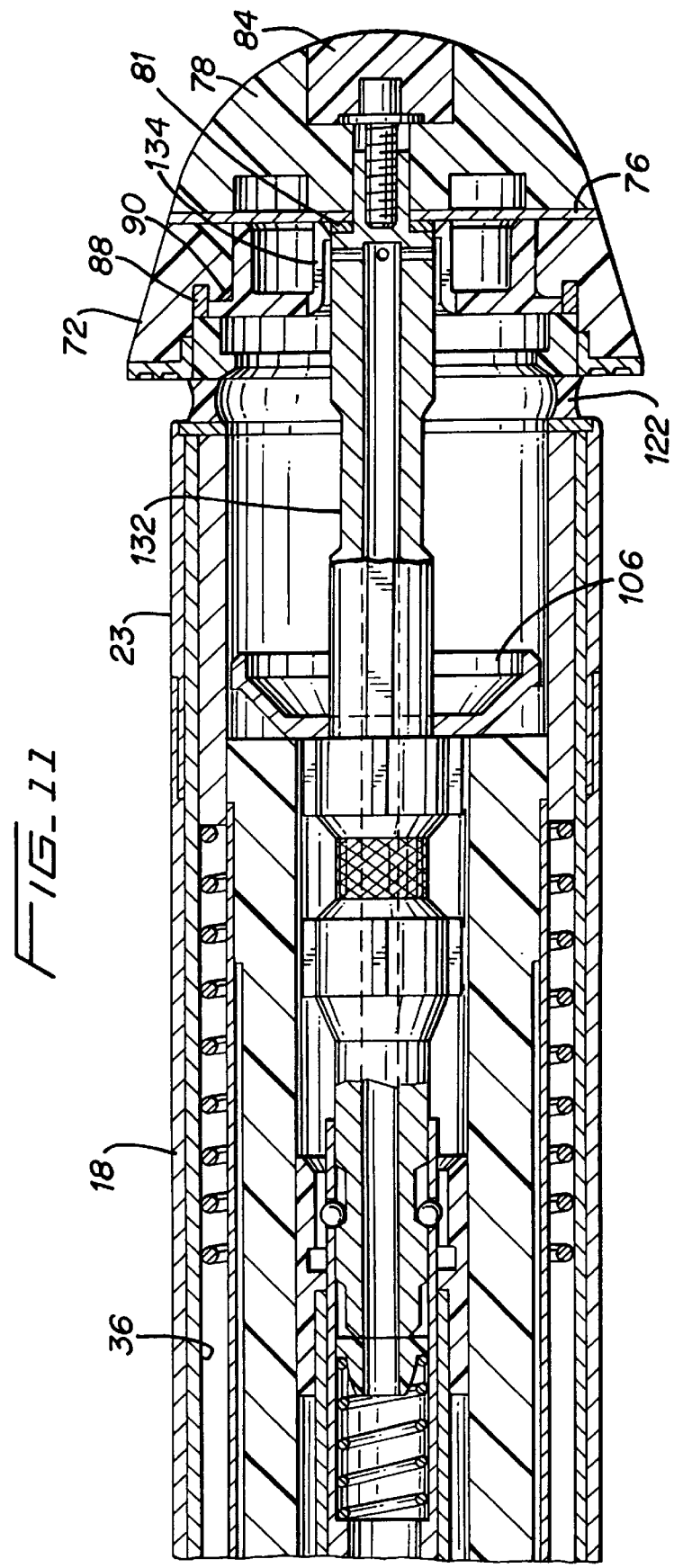

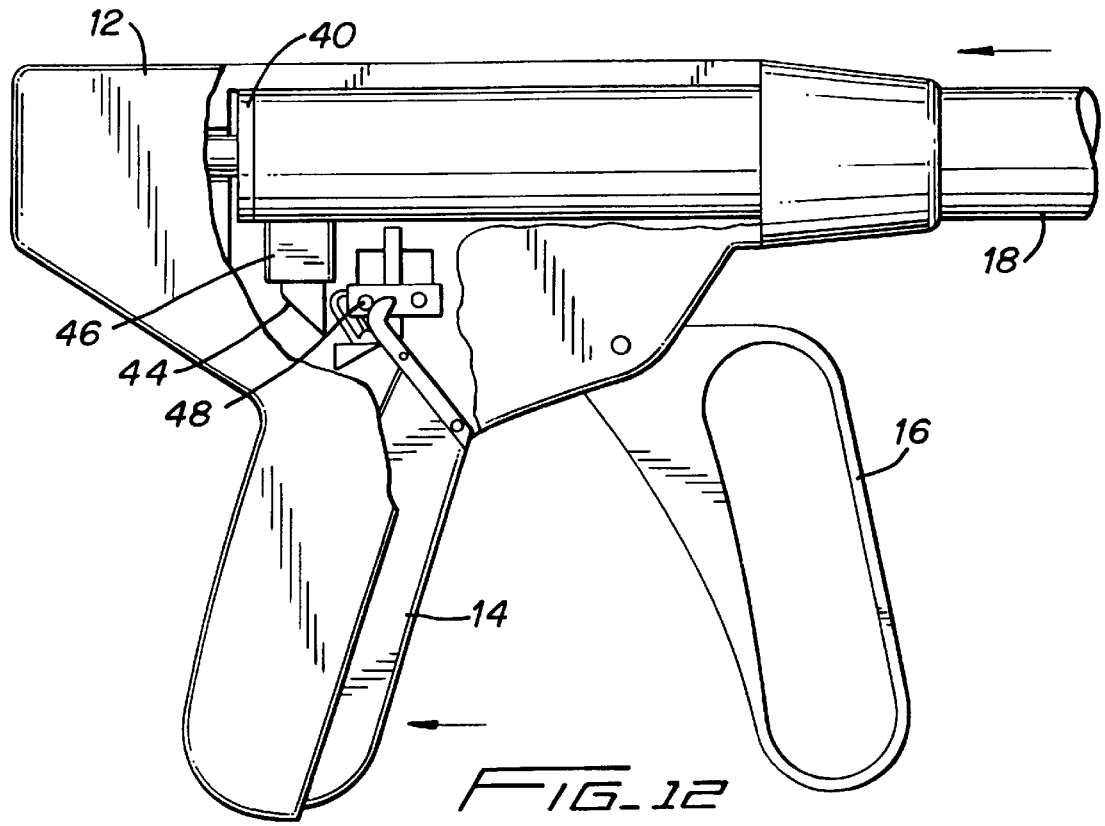
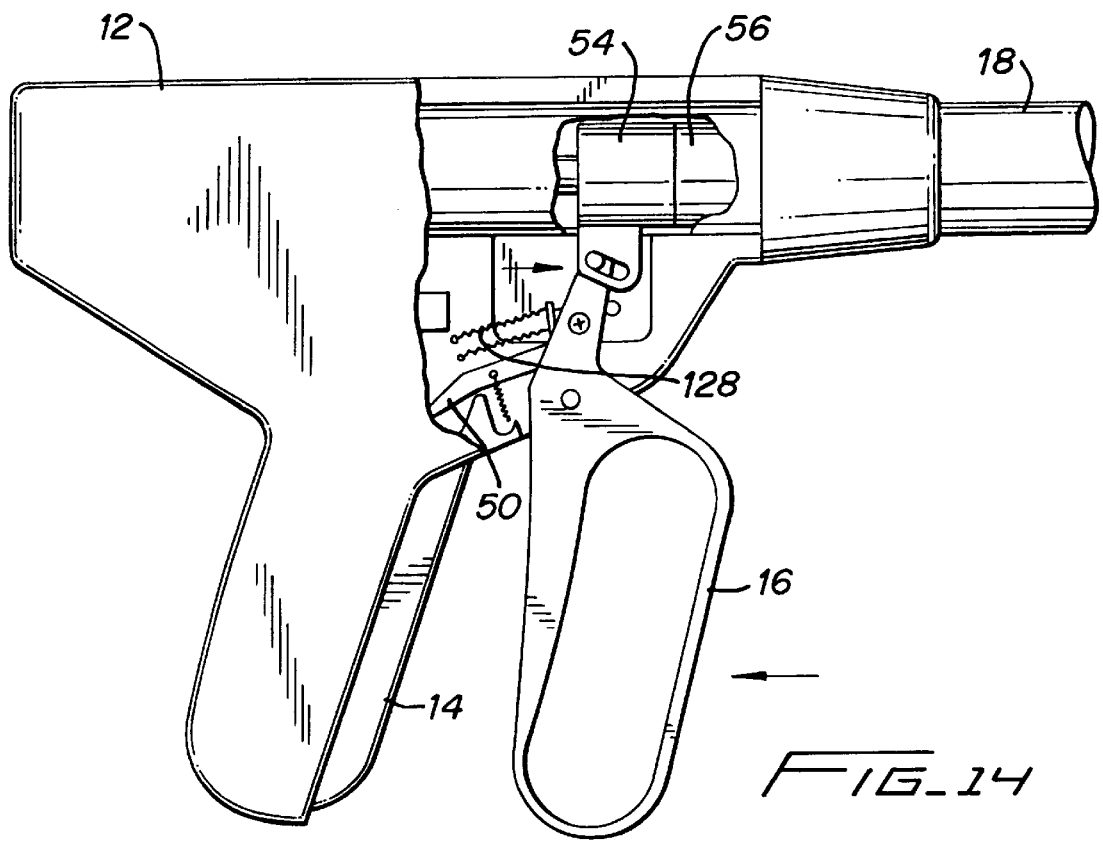

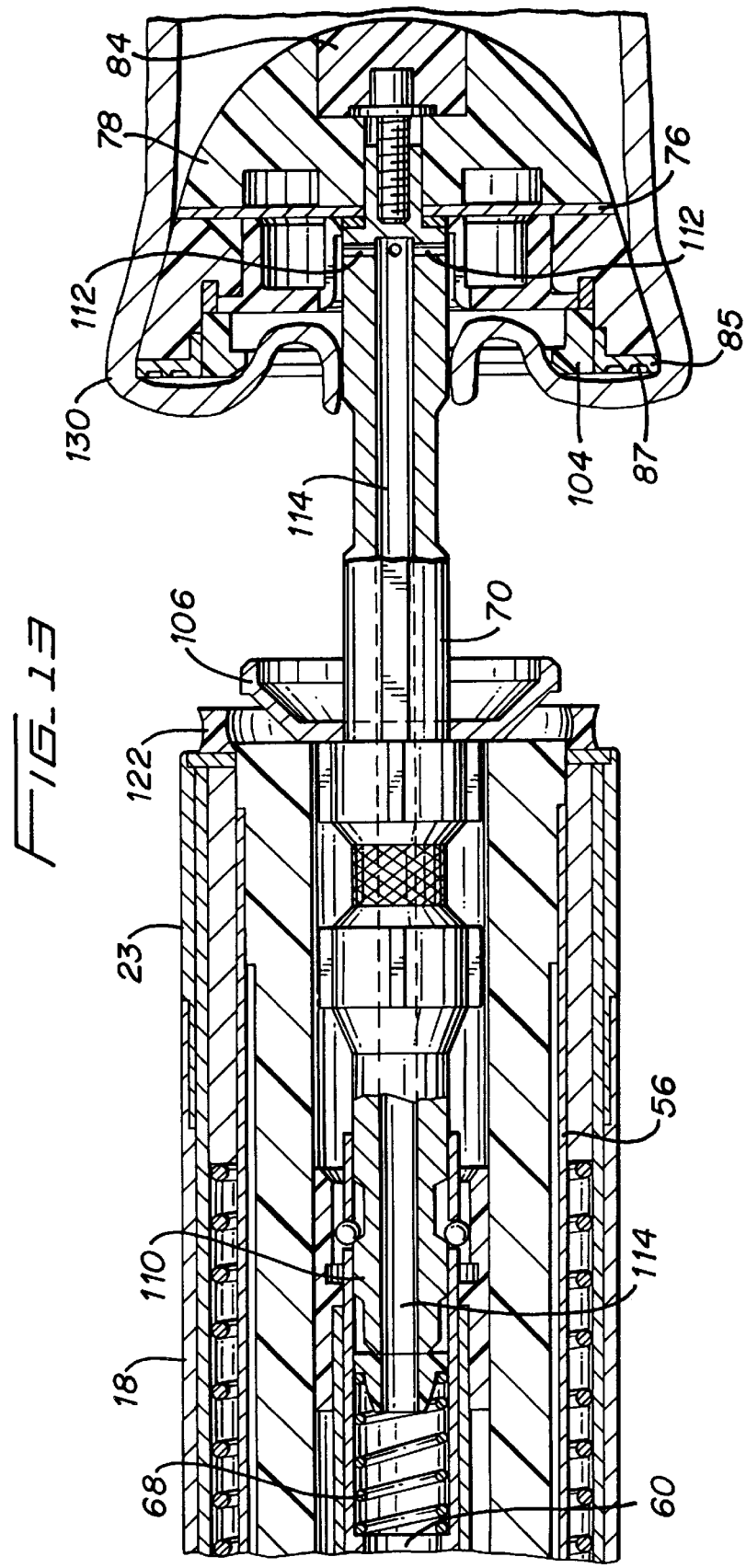

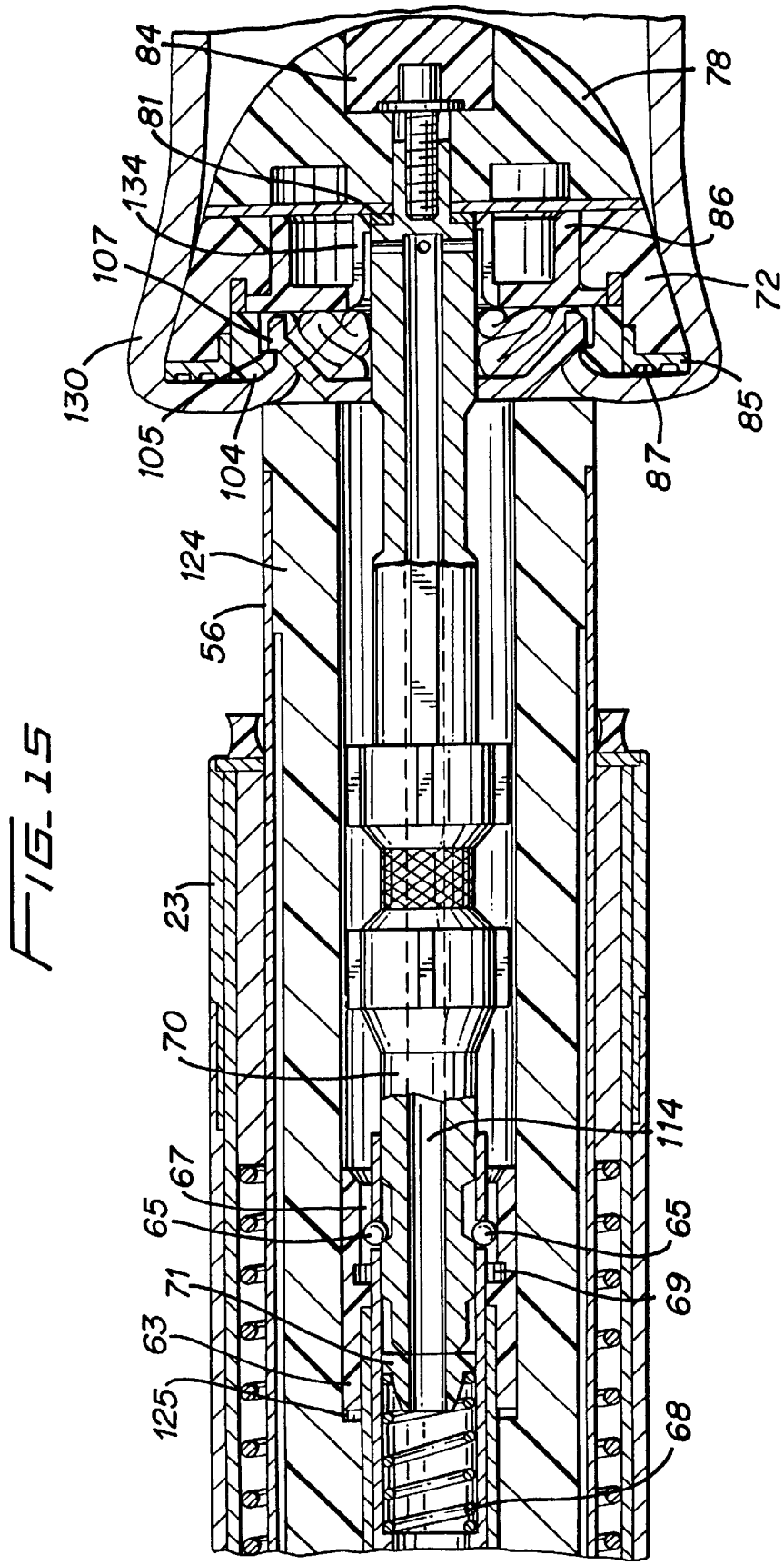

COLLAPSIBLE ANVIL ASSEMBLY AND APPLICATOR INSTRUMENT

BACKGROUND OF THE INVENTION

1. Field of the Invention

This invention relates to a surgical stapler apparatus. More particularly, this invention relates to a stapler anvil assembly for an end-to-end anastomosis stapler apparatus. Still more particularly, this invention relates to a collapsible anvil assembly and applicator instrument for a surgical stapler apparatus.

2. Discussion of the Related Art

Various types of surgical stapler apparati are known for the application of staples to tissue. For example, it is known to use various types of staplers in gastric and esophageal surgery, for example in both classic or modified gastric reconstructions performed end-to-end, end-to-side, or side-to-side. In some cases, it has been known to create an anastomosis utilizing an instrument such as that disclosed in U.S. Pat. No. 5,119,983, and manufactured by United States Surgical Corporation, wherein an anvil assembly can be positioned on the end of a center rod which is retracted within a tubular housing of the instrument. In some cases, such an instrument is introduced into the lumen of a stomach without the anvil in place. Thereafter, the tip of the center rod is passed through an opening which has been made at the anastomotic site so that the anvil can then be secured on the end of the center rod. Subsequently, the anvil can be inserted into the duodenum for securement to the center rod and the end of the duodenum is then tied off about the center rod, for example by a purse string suture. Thereafter the center rod is retracted towards the instrument to clamp the tissue between the anvil and the staple cartridge in order to position the instrument to fire the staples from the instrument into the anvil so as to join the stomach to the duodenum positioned therebetween. Typically, the anvil and stapler are introduced into the body during open surgery through a relatively large incision with all the attendant trauma to tissue and associated complications. While it is known to use detachable anvils for remote placement of the anvil within a patient's body, the insertion of the detachable anvil into the patient's body is still typically performed through a relatively large incision during open surgery. Other examples of anvils which are capable of collapsing to a reduced diameter after stapling to facilitate removal from the body are shown in U.S. Pat. Nos. 4,752,024 and 4,893,622 to Green et al. and U.S. Pat. Nos. 4,700,703 and 4,903,697 to Resnick et al. However, these anvils are also introduced into the body through a relatively large incision.

Generally, the tissue stapled together leaves a smaller opening than the original lumen into which the anvil and stapler were inserted. Frequently, it is desirable to provide an anvil which can be collapsed to introduce the anvil into the body through a relatively small incision. An example of a surgical stapler having a variable diameter anvil is illustrated in U.S. Pat. No. 4,505,414 to Filipi. Filipi discloses an anvil, integral with a surgical stapler, which can be collapsed and inserted through a small incision in a patient's body and expanded outwardly after placement inside the patient's body to staple the wall of an organ to the abdominal wall or an external tissue layer of the patient's body. The Filipi anvil is not detachable from the stapler and thus cannot provide a continuous staple line, but rather applies a broken, discontinuous line to "tack" the tissue in a circular line. Filipi also does not provide an anvil which can be placed remotely within the body for subsequent attachment to a stapler apparatus.

Therefore, it would be highly desirable to have a detachable and collapsible anvil assembly for the application of a continuous line of staples, and an applicator instrument which allows for remote placement of the anvil assembly into a patient's body either rectally or laparoscopically rather than through a comparatively large incision, in order to position the anvil within the body in limited accessibility applications for subsequent attachment to a circular surgical stapler also inserted either rectally or laparoscopically.

Accordingly, it is an object of the present invention to provide an anvil assembly and applicator instrument which allows for remote placement of the anvil assembly by insertion through a small incision in the body.

Another object of the present invention is to provide a collapsible anvil assembly having a flexible anvil segment along with immobilizing means for maintaining the anvil segments in a fixed, expanded configuration.

Another object of the present invention is to provide an anvil assembly which has means for attracting and holding a surrounding tissue section against staple clinching buckets of the anvil assembly without the need for an external purse string device or procedure.

An additional object of the present invention is to provide an anvil assembly which is detachable from an applicator instrument to facilitate remote placement of the anvil assembly within the body and subsequent attachment to a circular stapler.

Other and further objects of the present invention will be explained hereinafter, and will be more particularly delineated in the appended claims, and other objects of the present invention will hereinafter become apparent to one of ordinary skill in the art to which the present invention pertains.

SUMMARY OF THE INVENTION

The present invention is a collapsible anvil assembly for use with a surgical stapler and an applicator instrument for positioning the anvil in a patient's body for subsequent connection to the surgical stapler. The applicator instrument allows for laparoscopic or rectal placement of the anvil assembly, in a collapsed or reduced diameter configuration, within a patient's body. The collapsible anvil assembly includes an anvil shaft and a plurality of anvil segments, having staple clinching buckets thereon, flexibly affixed to the anvil shaft. The anvil segments are movable between a collapsed or radially inwardly deflected condition and an expanded or radially outwardly deflected condition for insertion in the collapsed condition and subsequent expansion. The applicator instrument is dimensioned and configured to hold the anvil segments in the collapsed condition and provides for the release of the segments for expansion. The applicator also provides for disengagement of the anvil to permit connection of the anvil to a surgical stapler.

Immobilizing means in the form of an axially slidable locking ring is provided to fix and maintain the anvil segments in the expanded condition. Means are also provided for detaching or ejecting the anvil assembly from the applicator instrument once the anvil assembly has been positioned within the patient's body. Preferably, the anvil segments include at least two segments having unequal arcuate length to facilitate maintaining the segments in a collapsed condition. Notches on the anvil segments are engagable with the locking ring to maintain the segments in the expanded condition.

Mounting means are also provided on the anvil shaft for subsequent detachable mounting of the anvil assembly on a surgical stapler. Alignment means are also provided on the shaft to ensure correct alignment of the anvil clinching buckets with the staples in the attached surgical stapler.

In a preferred embodiment of the collapsible anvil assembly and applicator instrument there is provided an novel purse stringing device which includes a plurality of suction holes on the anvil shaft to attract and hold a surrounding tissue section within the anvil segments. Additionally, an axially slidable tissue holding ring or snap cap is provided to lock the held tissue section within the anvil segments. Means are provided on the applicator instrument for providing a source of suction or vacuum to the anvil and for advancing the snap cap into engagement with the anvil assembly.

BRIEF DESCRIPTION OF THE DRAWINGS

For a further understanding of the present invention, reference is made to the following detailed description of the preferred embodiment which is to be taken in connection with the accompanying drawings, wherein:

FIG. 1 is a perspective view of the applicator instrument and collapsible anvil assembly of the present invention with the collapsible anvil assembly in a radially inwardly deflected condition and loaded into a distal end of the applicator instrument;

FIG. 2 is an cross-sectional view of the handle portion of the applicator instrument taken along lines 2—2 of FIG. 1;

FIG. 2A is an end view of the outer tube release components;

FIG. 4 is a side elevation view, partly shown in section, of the handle portion of the applicator instrument in the prefired condition;

FIG. 5 is an cross-sectional view of the distal end of the applicator instrument taken along lines 5—5 of FIG. 1 showing the collapsible anvil assembly installed in the applicator instrument in a prefired condition;

FIG. 6 is a sectional view of the collapsible anvil assembly installed in the applicator instrument and taken along lines 6—6 of FIG. 5;

FIG. 8 is an enlarged cross-sectional view of the distal end of the applicator instrument showing the outer tube retracted and the anvil segments in an expanded or radially outwardly deflected condition;

FIG. 9 is an end view of the collapsible anvil assembly taken along the lines 9—9 of FIG. 8;

FIG. 11 is an enlarged cross-sectional view of the distal end of the applicator instrument illustrating the insertion of the axle and locking ring into the anvil segments;

FIG. 12 is a side elevation view, partly shown in section, of the handle portion of the applicator instrument illustrating the back trigger fully retracted and the outer and axle tubes returning to a proximalmost position;

FIG. 13 is an enlarged cross-sectional view of the distal end of the applicator instrument illustrating the anvil assembly placed within a tissue section and attracting the tissue within the anvil by application of a vacuum;

FIG. 14 is a side elevation view, partly shown in section, of the handle portion of the applicator instrument illustrating the front trigger being retracted to advance a snap ring tube;

FIG. 15 is an enlarged cross-sectional view of the distal end of the applicator instrument illustrating the insertion of a snap ring within the anvil assembly to capture the tissue section therebetween.

DETAILED DESCRIPTION OF THE PREFERRED EMBODIMENT

Figure 3:
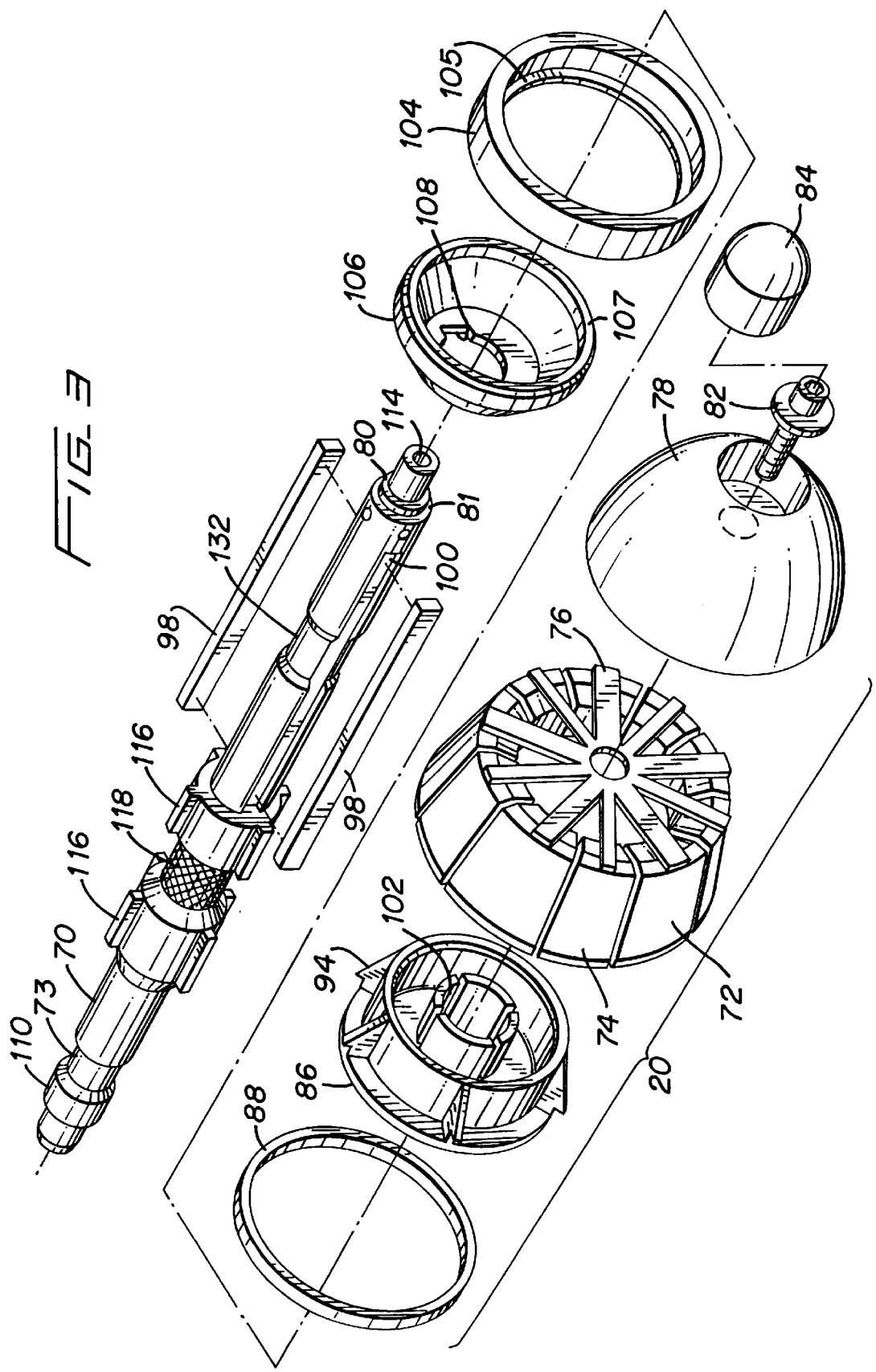
FIG. 3 is an exploded perspective view of the collapsible anvil assembly in accordance with the present invention.

Referring to FIGS. 1–16 wherein like parts have been given like index numerals and initially to FIGS. 1 and 3, there is shown a collapsible anvil assembly 20 and applicator instrument 10 in accordance with a preferred embodiment of the present invention. As shown in FIG. 1, collapsible anvil applicator 10 includes a handle housing 12 having a back trigger 14 and a front trigger 16. An outer tube 18 extends from a distal end of housing 12 and is axially movable relative thereto. Outer tube 18 is insertable through a small incision in a patient's body and has an outer diameter of approximately 1.0 inches (25.4 mm).

Collapsible anvil assembly 20 includes a plurality of radially deflectable anvil segments 21 and is configured to be mounted within a cartridge housing 23 to thereby form a detachable loading unit. Housing 23 maintains collapsible anvil assembly 20 within a distal end of outer tube 18 with anvil segments 21 in a collapsed or radially inwardly deflected configuration. When inserted, housing 23 is frictionally held within outer tube 18. As further shown in FIG. 1, applicator instrument 10 further includes a front trigger safety button 22 which is manually actuable to prevent inadvertent ejection of collapsible anvil assembly 20 as further described hereinbelow. Additionally, applicator instrument 10 is further provided with a vacuum connection 24 which can be used to connect anvil assembly 20 to a source of vacuum to aid in attracting tissue to anvil assembly 20 when anvil segments 21 are in an expanded or radially outwardly deflected state, as described below in detail. An end collar 26 may be provided on handle housing 12 to aid in guiding outer tube 18 during axial movement of outer tube 18.

A preferred embodiment of collapsible anvil assembly 20 in accordance with the present invention is best illustrated in FIGS. 3, 6 and 9. Collapsible anvil assembly 20 includes an anvil shaft 70 and a plurality of anvil segments 21. Preferably, anvil segments 21 radially alternate between large anvil segments 72 and small anvil segments 74. Anvil segments 72 and 74 are flexibly or deflectably connected to anvil shaft 70 by means of a flexible spoke hub 76. Alternately, segments 72 and 74 may be connected to shaft 70 by any flexible means, and may also be connected through means such as hinges. Anvil segments 72 and 74 alternately deflect radially inwardly to allow collapsible anvil assembly 20 to fit within housing 23 (FIG. 6) which is inserted within a distal end of outer tube 18 (FIG. 5). As shown in FIG. 5, a proximal end of housing 23 is frictionally held within, or press-fit into, a distal end of outer tube 18. An end cap 78 is provided to hold spoke hub 76 against an abutment 80 at a distal end of anvil shaft 70. A threaded fastener 82 secures end cap 78 on anvil shaft 70. As best shown in FIGS. 1, 3 and 5, an end plug 84 is provided to cover threaded fastener 82 and provide a smooth surface with respect to end cap 78 in order to reduce the chance of trauma to a tissue section during insertion of applicator instrument 20.

Typical circular staplers are provided with an annular array of surgical staples which can be driven into staple clinching buckets to fasten tissue positioned therebetween. Collapsible anvil assembly 20 is provided with a segmented staple clinching ring 85 affixed to proximal ends of anvil segments 72 and 74. Staple ring 85 is provided with a plurality of staple clinching buckets 87 as seen in FIGS. 6 and 9 which serve to clinch staples driven thereinto.

As noted above, anvil segments 72, 74 are radially deflectable in order to maintain collapsible anvil assembly 20 in a reduced diameter configuration for ease of insertion through a small incision. Once inserted and expanded, it is preferable to immobilize anvil segments 72 and 74 in order to advance staples into staple clinching buckets 87. Immobilizing means are provided in the form of an axle hub 86 which is mounted upon and axially slidable relative to anvil shaft 70. Axle hub prongs 134, as best seen in FIG. 8, formed on axle hub 86 engage a detent 132 on axle shaft 70 to hold hub 86 in an initial proximal most position. In a distal most position, axle hub prongs 134 engage an axle lip 81 formed on a distal end of anvil shaft 70, FIGS. 3 and 11. An axle hub locking ring 88 is affixed about axle hub 86. As shown in FIGS. 6 and 9, anvil segments 72 and 74 are provided with large and small latch notches 90 and 92, respectively. Axle locking ring 88 is designed to engage latch notches 90 and 92 to prevent any radial deflection of anvil segments 72, 74, as best seen in FIG. 11.

Referring to FIG. 3, axle hub 86 is provided with projections 94 to aid in guiding the advancement of axle hub 86 and thus locking ring 88 into engagement with anvil segments 72 and 74. As best shown in FIGS. 6 and 9, anvil segments 74 are preferably provided with two anvil latch notches 92 which define a gap or slot 96 therebetween. With reference to FIG. 3, shaft keyways 98 mounted in slots 100 on anvil shaft 70 serve to guide axle hub projections 94 into engagement with slots 96 on small anvil segments 74 by providing a predetermined alignment of the hub 86 on the shaft 70 with respect to segments 72 and 74. Axle hub 86 rides on keyways 98 by engagement with axle hub notches 102 on axle hub 86.

Referring back to FIGS. 2 and 2A, outer tube 18 is axially movable in order to hold and release anvil segments 21, contained within housing 23, between collapsed and expanded states. Referring now to FIG. 2, 2A and 4, it can be seen that an outer tube latch 31 initially holds outer tube 18 in a distal most direction, against the bias of a tube return spring 126 (FIG. 5), to hold anvil segments 21 in a collapsed condition. To release outer tube 18, back trigger 14 is pulled proximally. As back trigger 14 begins to be retracted a pin 30 rides along angled face 32 of outer tube release bar 28 pushing outer tube release bar 28 upwardly. As outer tube release bar 28 is moved upwardly it contacts a lower edge 33 of an outer tube latch 31 causing outer tube latch 31 to pivot about a pin 35. As outer tube latch 31 pivots it disengages from a notch 37 in outer tube 18 thereby freeing outer tube 18 for movement. A spring plate 39 is provided to press against a flat 41 on pivot pin 35 thereby holding outer tube latch 31 in a latched position until outer tube release bar 28 is pushed upwardly. When outer tube latch 31 is deflected it releases outer tube 18 allowing outer tube return spring 126 to force outer tube 18 proximally. As outer tube 18 moves proximally it draws housing 23 proximally thereby allowing anvil segments 72 and 74 to open.

Once anvil assembly 20 has been positioned within a tissue section, it is desirable to immobilize the opened anvil segments against any further radial deflection. An axially movable axle tube 36 is disposed within outer tube 18 and is provided to drive immobilizing means (as seen and described with respect to FIGS. 8 and 11) into engagement with anvil segments 21 to maintain anvil segments 21 in a radially outwardly deflected configuration. Referring back to FIG. 2, a carriage tube 38 affixed to a distal end of axle tube 36 has a circumferential flange 40 configured to engage a distal end of outer tube 18. A carriage 42 having an angled face 44 is affixed to an underside of carriage tube 38 to move axial tube 36. Back trigger 14 is provided with a back trigger pin 48 for engagement with angled face 44 of the carriage 42 to actuate the immobilizing means as back trigger 14 is drawn rearwardly. Carriage 42 contains a centered slot 46 extending longitudinally therethrough to allow pin 48 to move through carriage 42 to release pin 48 from carriage 42 and thus disengage back trigger 14 from carriage 42.

In addition to manual front trigger safety button 22, an automatic safety 50 is provided to prevent movement of front trigger 16 until back trigger 14 has been fully retracted. A tab 53 on a distal end portion of auto safety 50 engages a slot 52 in front trigger 16 to block front trigger 16 from being moved until auto safety 50 is disengaged. When back trigger 14 has been fully retracted, a strike plate 55 contacts a proximal end 51 of auto safety 50 to pivot tab 53 out of engagement with slot 52 thereby freeing front trigger 16 for movement. Front trigger 16 is provided to actuate the automatic purse stringing device and is pivotally mounted on frame housing 12. Front trigger 16 is connected at one end to a drive yoke 54 which is connected to a snap, or locking, ring tube 56. Snap ring tube 56 is provided to cooperate with the automatic purse stringing device once the collapsible anvil assembly 20 has been positioned and expanded within a tissue section.

In addition to actuating the automatic purse stringing device, front trigger 16, upon full retraction, ejects collapsible anvil assembly 20 from applicator 10 in a manner above fully described in detail hereinbelow. Still referring to FIG. 2, and as noted hereinabove, front trigger safety button 22 prevents ejection of anvil assembly 20 until button 22 is depressed. Button 22 has a safety shaft 25 extending transversely through frame 12. Safety shaft 25 has a larger diameter portion 27 which contacts a distal face of front trigger 16 thereby blocking front trigger 16 from being fully retracted. Depressing button 22 moves larger diameter portion 27 of safety shaft 25 out of the way of front trigger 16, allowing front trigger to be fully retracted to eject collapsible anvil assembly 20 from applicator 10.

Referring now to FIGS. 2, 5 and 6, collapsible anvil assembly 20 is initially disposed in a collapsed condition within housing 23 prior to loading within applicator 10. To load collapsible anvil assembly 20, contained within housing 23, within applicator instrument 10 there is provided a quick release mechanism for releaseably securing anvil assembly 20 therein. Referring to FIG. 2 quick release mechanism generally includes a shaft release tube 62, which surrounds an air delivery tube 60, and an anvil load button 64 abutted to a proximal end of shaft release tube 62. As most clearly seen in FIG. 8, a distal end of shaft release tube 62 is connected to a ball release collar 63 which surrounds a plurality of releasing balls 65. Preferably ball release collar 63 is provided with areas of varying internal diameter to move releasing balls 65 radially inwardly and outwardly. The areas of varying internal diameter generally include a reduced diameter portion 67 and a larger diameter portion 69. Releasing balls 65 are positioned within corresponding holes 61 extending through air delivery tube 60. To load collapsible anvil assembly 20 and housing 23 within applicator instrument 10, anvil load button 64 is depressed thereby driving shaft 62 and ball release collar 63 distally allowing releasing 65 balls to move radially outwardly into large diameter portion 69 of release collar 63. Note that anvil preload spring 66 provides a preload to maintain anvil button 64, and therefore ball release collar 63, in a normally proximal most position.

Insertion of collapsible anvil assembly 20 within applicator instrument 10 causes anvil shaft 70 to move an anvil eject bushing 71 (FIG. 15) proximally thereby compressing anvil eject spring 68. As anvil load button 64 is released, ball release collar 63 moves proximally causing reduced diameter portion 67 to override balls 65 forcing balls 65 radially inwardly through holes 61 in shaft 60 to thereby lock against a chamfered surface 73 of anvil shaft 70. As collapsible anvil assembly 20 is being inserted into applicator 10, housing 23 engages outer shaft 18 and is held therein in friction fit fashion. Thus applicator instrument 10 is loaded with a detachable loading unit "DLU" consisting of collapsible anvil assembly 20 and anvil housing 23 and is now suitable for us in various procedures. Applicator instrument 10 and collapsible anvil assembly 20 may be provided assembled or separately.

As noted above, applicator instrument 10 is capable of connection to a vacuum source to assist in drawing tissue against collapsible anvil assembly 20. Referring to FIG. 2, applicator instrument 10 includes a vacuum passage 58 which extends between the vacuum connection port 24 and an air delivery tube 60 located axially within applicator instrument 10. Air delivery tube 60 serves to provide a source of vacuum or suction to the collapsible anvil assembly 20.

Referring to FIG. 3, the automatic purse stringing feature of collapsible anvil assembly 20 includes a snap cap pocket 104 which is affixed to a proximal end of axle hub 86. A snap cap 106 is axially slidable along anvil shaft 70 and is guided thereon by means of notches 108 which ride on shaft keyways 98. Snap cap 106 is provided to engage and capture tissue between snap cap 106 and snap cap pocket 104. A lip 105 on snap cap pocket 104 is adapted to engage an edge 107 of snap cap 106 to hold snap cap 106 firmly within snap cap pocket 104. Preferably, a proximal surface of snap cap pocket 104 forms a surface against which knife means on a surgical stapler can abut to sever tissue positioned therebetween.

The automatic purse string feature of the collapsible anvil assembly is aided, as noted hereinabove, by providing a source of suction to collapsible anvil assembly 20 in order to draw tissue against anvil segments 21 and between snap cap pocket 104 and snap cap 106. Vacuum holes 112 are provided radially at a distal end of anvil shaft 70 and are communicable with a central bore 114 of anvil shaft 70. A front air seal (not shown) located distal to anvil eject bushing 71 is provided to compress against mounting projection 110 and thus seal bore 114 in fluid communication with air delivery tube 60.

After anvil segments 21 have been expanded and immobilized, and the automatic purse stringing feature activated, it is desirable to eject anvil assembly 20 from applicator instrument 10.

Collapsible anvil assembly 20 is detachable from applicator 10 to permit use with various circular stapling instruments. As noted hereinabove collapsible anvil assembly 20 is held in place on applicator instrument 10 by engagement of balls 65 with chamfered surface 73 of anvil shaft 70.

Referring now to FIGS. 2 and 8, to release collapsible anvil assembly 20 from applicator instrument 10, front trigger safety button 22 is depressed thereby allowing front trigger 16 to be fully retraced as described in more detail hereinabove. Full retraction of front trigger 16 drives snap ring tube 56 distally thereby driving snap cap pusher 124 to a distal most position. As snap cap pusher 124 is driven distally a proximal shoulder 125 of snap cap pusher 124 engages ball release collar 63 driving ball release collar 63 forward. As ball release collar 63 is driven forward, balls 65 extend into larger diameter portions of ball release collar 63 thereby freeing anvil 70. Anvil 70 is ejected from the instrument as anvil eject bushing 71 moves forward against the bias of compressed anvil eject spring 68. It will be noted that after collapsible anvil assembly 20 has been ejected from applicator instrument 10, housing 23 remains in a frictionally held fashion within outer tube 18 and may be removed manually for insertion of a new DLU. Anvil assembly 20 includes a mounting projection 110 which is adapted to engage corresponding mounting means on the center rod of the circular surgical stapler.

In connecting detachable anvil assembly 20 to a circular surgical stapler, it is necessary to ensure correct alignment of the annular array of staples within the stapler head with staple clinching buckets 87. Referring to FIG. 3, collapsible anvil assembly 20 includes alignment means in the form of alignment collars 116 affixed to anvil shaft 70. Projections 94 on axle hub 86 engage gap 96 on small anvil segments 74 to ensure correct alignment of the staple clinching buckets 87 relative to anvil shaft 70. Collars 116 on anvil shaft 70 align staple clinching buckets 87 with staples, in the stapler, when the anvil assembly is mounted on a circular surgical stapler.

Further, to facilitate manipulation of collapsible anvil assembly 20 within an organ, particularly during a laparoscopic procedure, it may be necessary to utilize laparoscopic grasping tools having an elongated body extending from a handle and terminating in a grasping tool mechanism. To aid in the grasping of the anvil by the grasping tool, collapsible anvil assembly 20 includes a knurled surface 118 on shaft 70 positioned between alignment collars 116. Knurled surface 118 aids in grasping and manipulation of anvil shaft 70 once anvil assembly 20 has been positioned within the body and ejected from applicator instrument 10.

The operation of the collapsible anvil assembly 20 and collapsible anvil applicator 10 is best illustrated in FIGS. 1 and 4–15. Referring initially to FIG. 1, and as noted above, collapsible anvil assembly 20 is initially positioned within housing 23 in a collapsed or radially inwardly deflected condition and mounted within a distal end of outer tube 18 as described hereinabove. An incision is made in the body at a location remote from the desired position of the anvil assembly and collapsible anvil applicator 10 is inserted therethrough.

Collapsible anvil assembly 20, in a collapsed condition, can thereafter be positioned at a desired location, such as, for example, in a resected bowel section.

Figure 7:
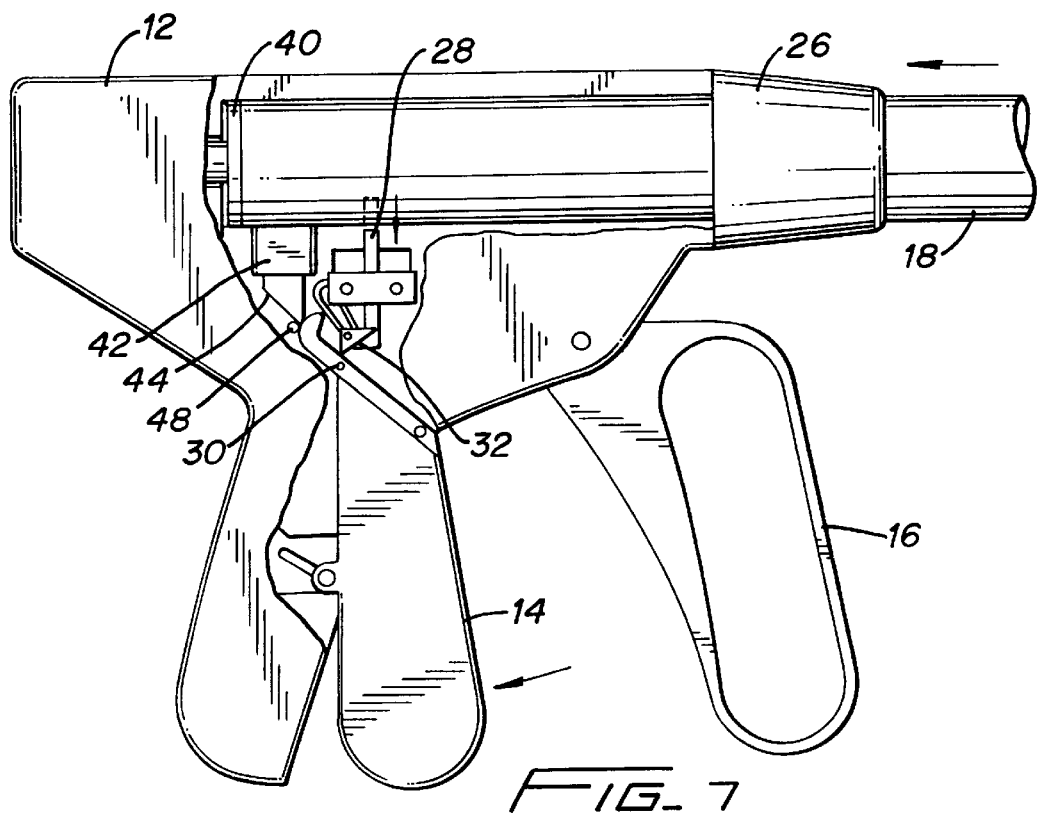
FIG. 7 is a side elevation view, partly shown in section, of the handle portion of the applicator instrument showing the back trigger partially retracted to release the outer tube.

Referring now to FIG. 4, in a prefired state, it can be seen that front trigger 16 and back trigger 14 are initially disposed in a forward or distalmost position. Outer tube 18 is held in a distalmost position about collapsible anvil assembly 20 by means of outer tube release bar 28. Collapsible anvil assembly 20 is maintained in position at a distal end of the applicator instrument 10 by means of housing 23 and outer tube 18. Balls 65 engage chamfered surface 73 of anvil shaft 70 to hold collapsible anvil assembly 20 on applicator 10 as shown in FIG. 5. Preferably, as shown in FIG. 6, anvil segments 72 and 74 are maintained in the collapsed condition with small anvil segments 74 positioned radially inwardly of large anvil segments 72. As further shown in FIG. 6, the positions of anvil segments 72 and 74 are contained within an outer circumference of end cap 78. Referring now to FIGS. 2, 2A and 7, as back trigger 14 is initially pivoted rearwardly, pin 30 engages angled face 32 on outer tube release bar 28 thereby driving outer tube latch 31 out of engagement with notch 37 in outer tube 18. Once outer tube latch 31 is disengaged from outer tube 18, outer tube 18 is moved proximally due to the bias of spring 126 (FIG. 8) drawing housing 23 proximally. As outer tube 18, and thus housing 23, reaches a proximalmost position with a distal end of outer tube 18 abutting flange 40, anvil segments 72 and 74 are free to deflect radially outwardly due to the bias of spoke hub 76. As best shown in FIGS. 8 and 9, after anvil segments 72 and 74 are deflected radially outwardly, staple ring 85 forms a continuous annular array of staple clinching buckets 87.

Figure 10:
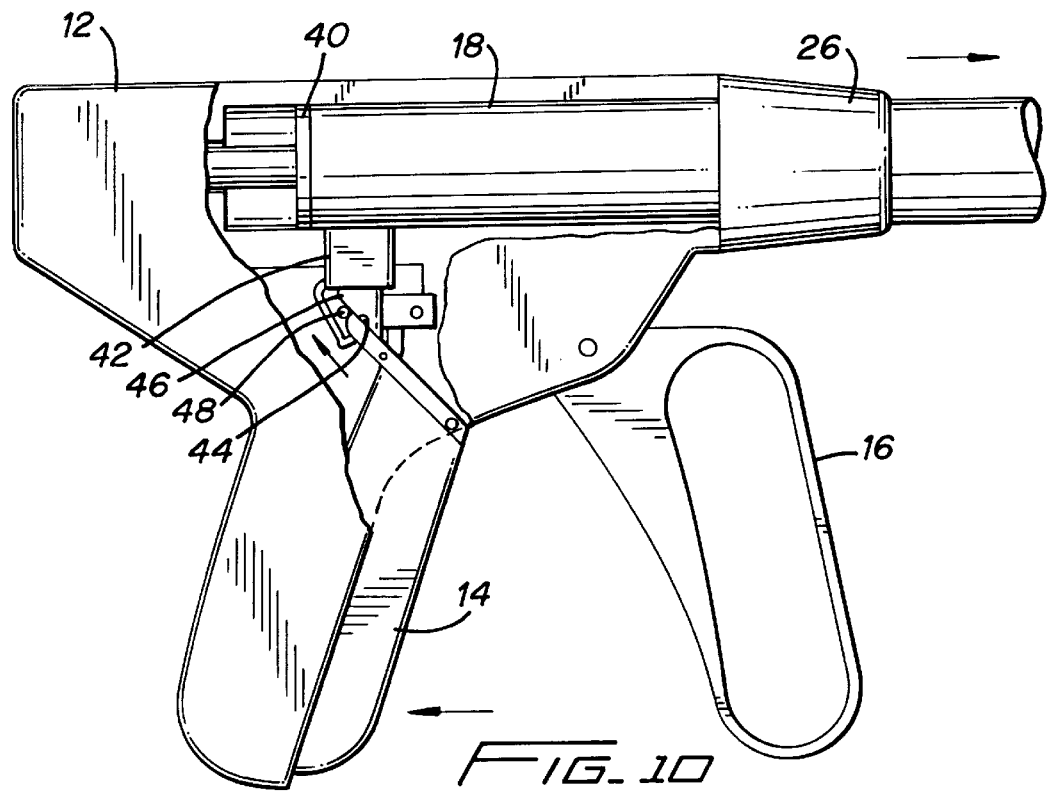
FIG. 10 is a side elevation view, partly shown in section, of the handle portion of the applicator instrument with the back trigger further retracted to advance the axle and outer tubes.

As noted above, it is desirable to immobilize the anvil segments to prevent any deflection during stapling. Referring now to FIG. 10, as rear trigger 14 is pivoted further, pin 48 on trigger 14 rides up angled face 44 driving carriage 42 distally. As carriage 42 is driven distally, it moves carriage tube 38 (FIG. 2) and thus axle tube 36 distally. Carriage tube flange 40 moves outer tube 18 distally. Referring now to FIGS. 8 and 11, as outer tube 18 and axle tube 36 are driven distally, a load ring 122 positioned at a distal end of axle tube 36 advances axle hub 86 towards anvil segments 72 and 74. Axle hub 86 carries axle locking ring 88 into engagement with latch notches 90 and 92 on anvil segments 72 and 74, respectively, to thereby immobilize the anvil segments in an open position. As noted above and shown in FIGS. 3, 6 and 9, projections 94 on axle hub 86 engage gap 96 between small anvil segment notches 92 to ensure proper alignment of the anvil clinching buckets with respect to the anvil shaft 70.

Referring now to FIG. 12, as rear trigger 14 is pivoted further, pin 48 engages slot 46 in carriage 42 and rides through slot 46 in carriage 42 to thereby release carriage 42 from rear trigger 14. As carriage 42 is released from trigger 14, an axle tube return spring 127 (FIG. 5) moves axle tube 36, and thus carriage tube 38, proximally thereby drawing load ring 122 away from axle hub 86. Note that at the same time spring 126 drives outer tube 18 to a proximal most position.

Once anvil assembly 20 has been positioned within a tissue section, such as the resected bowel section, and flexible anvil segments 72 and 74 have been immobilized by insertion of locking ring 88, it is desirable to secure the tissue section against anvil assembly 20. As noted hereinabove, one known method of securing a surrounding tissue section to an anvil shaft involves the use of a purse string device and sutures to tie off a section of tissue about the anvil shaft.

Collapsible anvil assembly 20 and applicator instrument 10 are provided with a novel automatic purse stringing device in the form of a vacuum source and snap cap arrangement. Referring to FIGS. 2 and 13, a source of vacuum can be connected to vacuum connection 24 and turned on by any suitable means. Once the vacuum is turned on, it creates a source of vacuum through vacuum passage 58 and thus through air delivery tube 60. As noted above, bore 114 of anvil shaft 70 is sealingly engaged with air delivery tube 60 by means of a front air seal (not shown). Once the vacuum source has been turned on, it draws air through vacuum holes 112 drawing the surrounding tissue sections inwardly against axle hub 86.

Once the surrounding tissue section has been drawn against axle hub 86, snap cap 106 can be advanced as described with reference to FIGS. 14 and 15 below to lock the tissue section between snap cap 106 and snap cap pocket 104. As noted above, after back trigger 14 has been drawn fully rearwardly, it disengages auto safety 50 from slot 52 in front trigger 16. Once auto safety 50 has been disengaged from front trigger 16, trigger 16 is free for pivotable movement.

Referring now to FIGS. 2, 14 and 15, when rear trigger 14 reaches a proximal most position strike plate 55 engages proximal end 51 of auto safety 50 to pivot tab 53 out of engagement with slot 52 in front trigger 16. Front trigger 16 is thus released for movement. Upon drawing front trigger 16 rearwardly, drive yoke 54 and thus snap ring tube 56 are driven distally. Initially, snap cap 106 is in a proximalmost position abutting an alignment collar 116. Axle hub 86 is positioned adjacent axle lip 81 and axle hub prongs 134 extend into axle lip 81. Snap cap pusher 124, affixed to a distal end of snap cap tube 56, drives snap cap 106 towards and about tissue sections positioned within axle hub 86. As noted above, an edge 107 of snap cap 106 engages a lip 105 of snap cap pocket 104 to firmly secure snap cap 106 within snap cap pocket 104. In this manner, the tissue section has automatically been securely fastened to the anvil segment in preparation for stapling and no outside or additional purse string suturing operation is necessary.

After inserting and fastening the collapsible anvil assembly to a tissue section, it is desirable to disengage the collapsible anvil assembly from the applicator instrument. By depressing safety button 22 front trigger 14 is free to move to a proximalmost position driving proximal shoulder 125 of snap cap pusher 124 into engagement with ball release collar 63. As releasing balls 65 move radially outwardly, anvil 70, and thus collapsible anvil assembly 20, is ejected from applicator instrument 10 by means of anvil eject spring 68.

Figure 16:
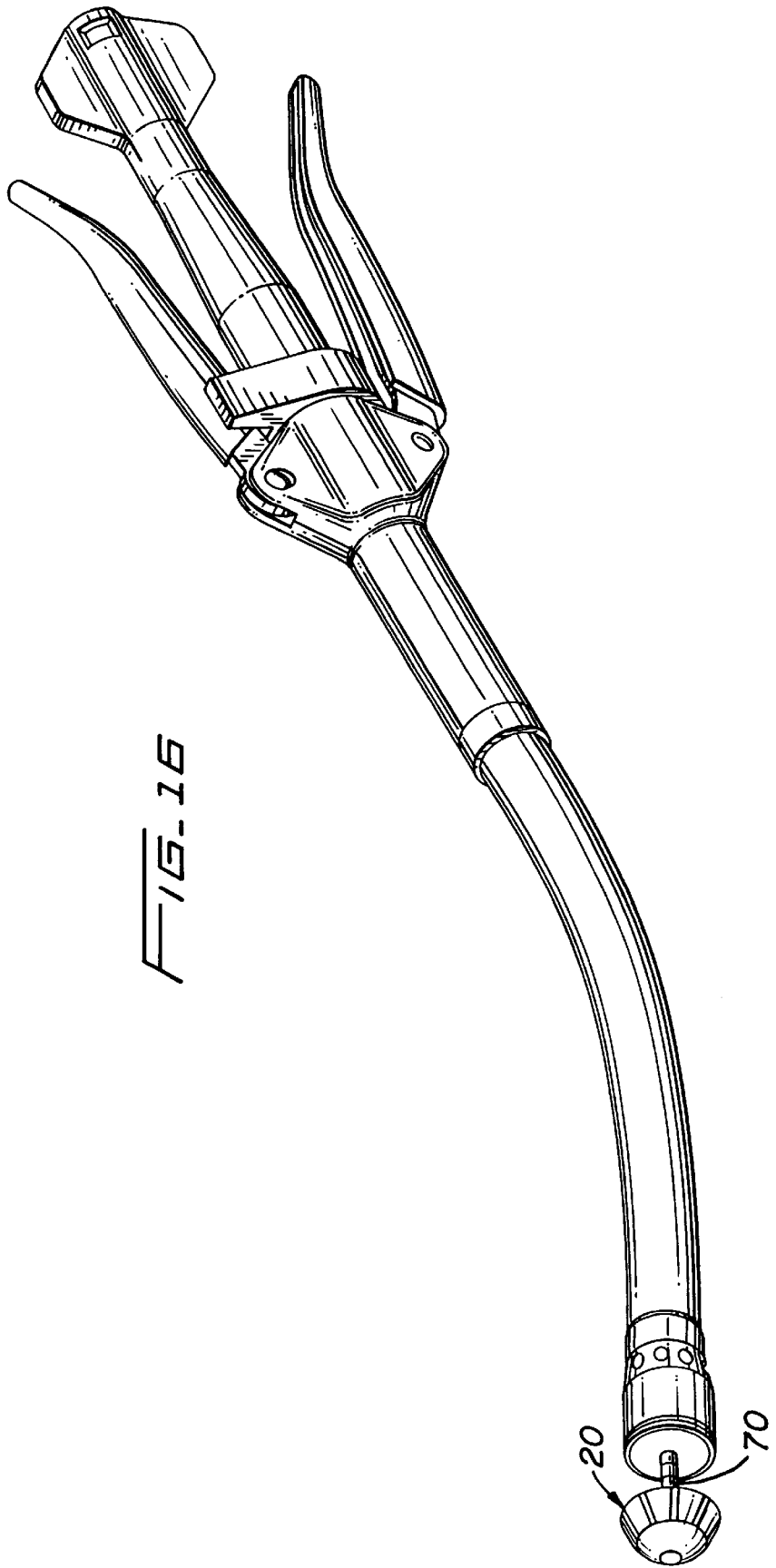
FIG. 16 is a perspective view of a circular stapling instrument, suitable for use with the collapsible anvil assembly of the present invention, with the collapsible anvil assembly installed thereon.

At this stage, a circular surgical stapler can be inserted through an opposing bowel section and connected to mounting means 110 of collapsible anvil 20 to provide for stapling the tissue sections together. As noted above, alignment collars 116 enable staple clinching buckets 87 to be properly aligned with the staples in the circular stapling instrument. A circular surgical stapler with a collapsible anvil assembly mounted thereon is illustrated in FIG. 16.

The invention in its broader aspects, therefore, is not limited to the specific embodiment herein shown and described but departures may be made therefrom within the scope of the accompanying claims without departing from the principles of the invention and without sacrificing its chief advantages.

What is claimed is:

1. An installation system for laparoscopic insertion of anvil assembly within a patient comprising:
   a) an anvil assembly having a shaft member, the shaft member having mounting means at a proximal end thereof and an anvil member affixed to a distal end of said shaft member, said shaft member having an axial bore therein and a plurality of suction orifices extending transversely through said shaft member, said suction orifices being communicable with said bore; and
   b) an installation tool member having a proximal end and a distal end, said installation tool member including means at said distal end for engaging said mounting means of said anvil assembly, and further including means for connecting said axial bore of said shaft member to a source of suction, such that when said source of suction is applied to said tool member, said suction causes a surrounding tissue section to be drawn against said suction orifices of said shaft member.

2. The installation system as recited in claim 1 wherein said anvil member includes a plurality of anvil segments flexibly affixed to said shaft member and defining a plurality of staple clinching buckets for clinching staples, said anvil segments being movable from a first position in which said segments are radially deflectable with respect to said shaft member to a second position in which said segments are immovable with respect to said shaft member, and immobilizing means axially slidable along said shaft member for maintaining said anvil segments in said second position; said installation tool further including deflecting means axially movable with respect to said installation tool for radially deflecting said anvil segments.

3. The installation system as recited in claim 2 wherein said installation tool further includes first actuation means for advancing said immobilizing means into engagement with said anvil segments.

4. The installation system as recited in claim 3 wherein said immobilizing means includes a locking ring axially slidable along said shaft member for maintaining said anvil segments in said second position; and said first actuation means includes a first actuation member adapted to advance said locking ring along said shaft member, said first actuation means further including first lever means at a proximal end of said frame for remotely moving said first actuation member.

5. The installation system as recited in claim 3 wherein said anvil assembly includes means to secure a tissue section against a proximal end of said anvil member.

6. The installation system as recited in claim 5 wherein said securing means includes a snap cap axially slidable along said shaft member; and said installation tool includes a second actuation member movable relative to said anvil member for advancing said snap cap against said proximal end of said anvil member.

7. The installation system as recited in claim 1 wherein said installation tool member further includes release means for disengaging said anvil assembly from said engaging means.

8. The installation system as recited in claim 7 further comprising remotely actuable means associated with said release means for ejecting said shaft member from said installation tool.

9. The installation system as recited in claim 7 wherein said shaft member mounting means is releasably engagable with said release means of said installation tool member.

10. An installation system for laparoscopic insertion of an anvil assembly within a patient comprising:

an anvil assembly having a shaft member with mounting means at a proximal end thereof and an anvil member at a distal end thereof;

a snap cap axially slidable along said shaft member for securing a tissue section against a proximal end of said anvil member; and, an installation tool member having a proximal end and a distal end, said installation tool member including means at said distal end for engaging said mounting means of said anvil assembly, said installation tool further having a first actuation member for advancing said snap cap against said proximal end of said anvil member.

11. The installation system as recited in claim 10 wherein the anvil member comprises a plurality of anvil segments flexibly affixed to said shaft member, the installation system further comprising immobilizing means axially slidable along said shaft member for maintaining said anvil segments in a position immovable with respect to said shaft member, the installation tool further comprising a second actuation member for advancing said immobilizing means into engagement with said anvil segments.

12. The installation system as recited in claim 10 wherein said shaft member has an axial bore therein and a plurality of suction orifices extending transversely through said shaft member, said suction orifices being communicable with said bore.

13. The installation system as recited in claim 12 wherein said installation tool further comprises means for connecting said axial bore of said shaft member to a source of suction.

14. An installation system for laparoscopic insertion of an anvil assembly in a patient, said installation system comprising:

a) an installation tool having a frame member;

b) an anvil assembly having mounting means at a proximal end of a shaft member of the anvil assembly for releasably holding said anvil assembly within said frame member;

c) release means associated with a proximal end of said frame member for remotely releasing said mounting means;

d) an axial bore within said shaft member; and e) a plurality of suction orifices extending transversely through said shaft member and communicable with said axial bore.

15. The installation system as recited in claim 14 further comprising means for connecting said axial bore of said shaft member to a source of suction.

16. An installation system for laparoscopic insertion of an anvil assembly within a patient comprising:

a) an anvil assembly having mounting means; and b) an installation tool member having a proximal end and a distal end, said installation tool member including means at said distal end for engaging said mounting means of said anvil assembly, and c) a circular stapler assembly including:

i) a frame member having means for mounting said anvil assembly;

ii) a staple carrying part containing staples at a distal end of said frame member; and iii) means for driving said staples from said staple carrying part towards said anvil assembly.

17. A surgical fastening device comprising:

a) a stapling instrument having an elongated body with a central bore therethrough; and b) an anvil member having a shaft and mounted at a distal end of said elongated body, said shaft having a central bore communicable with said central bore of said elongated body, said anvil member further having radial apertures extending between an outer surface of said shaft and said central bore of said shaft, wherein providing a source of vacuum to said central bore of said stapling instrument creates a vacuum in said radial apertures to draw a surrounding tissue section against said shaft.

* * * * *